United States Patent [19]

Darzynkiewicz et al.

[11] Patent Number: 5,747,258

[45] Date of Patent: May 5, 1998

[54] DETECTION OF HALOGENATED PRECURSORS INCORPORATED INTO DNA

[75] Inventors: Zbigniew D. Darzynkiewicz, Chappaqua; Xun Li, Yorktown Hights; Frank N. Traganos, New York; Myron R. Melamed, Dobbs Ferry, all of N.Y.

[73] Assignee: New York Medical College, Valhalla, N.Y.

[21] Appl. No.: 667,294

[22] Filed: Jun. 20, 1996

Related U.S. Application Data

[63] Continuation of Ser. No. 249,394, May 26, 1994, abandoned.

[51] Int. Cl.$^6$ .............................. C12Q 1/68; C12Q 1/02; G01N 21/75; G01N 21/76
[52] U.S. Cl. .............................. 435/6; 435/29; 436/124; 436/164; 436/172
[58] Field of Search .............................. 435/4, 5, 6, 29; 436/124, 164, 172

[56] References Cited

U.S. PATENT DOCUMENTS

| | | | |
|---|---|---|---|
| 4,780,406 | 10/1988 | Dolbear et al. | 435/6 |
| 4,851,331 | 7/1989 | Vary et al. | 435/6 |
| 5,053,336 | 10/1991 | Vanderlaan et al. | 435/240.27 |
| 5,084,378 | 1/1992 | Crissman et al. | 435/6 |
| 5,360,893 | 11/1994 | Owens et al. | 530/350 |
| 5,399,586 | 3/1995 | Davies et al. | 514/448 |
| 5,436,134 | 7/1995 | Haugland et al. | 435/34 |
| 5,464,833 | 11/1995 | Nakai et al. | 514/251 |
| 5,464,871 | 11/1995 | Kun et al. | 514/617 |
| 5,476,659 | 12/1995 | Goodman et al. | 424/278.1 |
| 5,484,951 | 1/1996 | Kun et al. | 549/285 |
| 5,500,432 | 3/1996 | Nicolaou et al. | 514/281 |
| 5,504,093 | 4/1996 | Gelfand et al. | 514/314 |
| 5,519,053 | 5/1996 | Kun et al. | 514/457 |
| 5,527,682 | 6/1996 | Owens | 435/6 |
| 5,539,094 | 7/1996 | Reed et al. | 536/23.5 |

OTHER PUBLICATIONS

Beisker et al. "Measurement of the Kinetics of DNA Repair Synthesis after UV Irradiation Using Immunochemical Stains of Incorporated 5–Bromo–2'–deoxyuridine & Flow Cytometry" Exp. Cell. Res. 174 156–167 1988.
Zucker et al. "Effect of Incorporation of 5–Iodo–2'–Deoxyuridine Into HBV–1 DNA On Virion Sensitivity to Ultraviolet Light" Biochem. Pharmacol. 36 (20) 3471–3476 1987.
Southern "Detection of Specific Sequences Among DNA Fragments Separated by Gel Electrophoresis" J. Mol. Biol. 98 503–517 1975.
Bayer et al. "The Use of *E coli* Exonuclease III to Generate Single Stranded DNA in BrdUrd Cell–Cycle Analysis Permit Simultaneous Detection of Cell Surface Antigens" J Immunol Meth 132 13–24 1990.

Glickman "The Role of DNA Polymerase I In Pyrimidine Dimer Excision & Repair Replication in *Escherichia coli* K12 Following Ultraviolet Irradiation" Biochim et Biophys Acta 335 116–122 1974.
Gratzner, H.G.:Monoclonal Antibody to 5–Bromodeoxyuridine. A New Reagent for Detection of DNA replication in *Science.* 218:474–475, 1982.
Dolbeare, F., H.G. Gratzner, M.G. Pallavicine and J.W. Gray.:Flow Cytometric Measurement of Total DNA Content and Incorporated Bromodeoxyuridine in *Proc Natl Acad Sci USA.* 80: 5573–5577, 1983.
Begg, A.C., N.J. Menally, D.C. Shrieve and H. Karchner.: A Method to Measure the Duration of DNA Synthesis and the Potential Doubling Time from a Single Sample in *Cytometry.* 6:620–626, 1985.
Falini, B., S. Canino, S. Sacchi, C. Ciani, M.F. Martelli, J. Gerdes, H. Stein, S. Pileri, M.Gobbi, M. Fagioloi, O. Minelli and L. Flenghi.:Immunocyctochemical Evaluation of the Percentage of Proliferating Cells in Pathological Bone Marrow and Peripheral Blood Samples with the Ki–67 and Anti–Bromodeoxyuridine Antibodies in *Br. J. Hematol.* 69: 311–320, 1988.
Williamson K., I. Halliday, P. Hamilton, J. Ruddell, M. Varma, P. Maxwell, A. Crockard and B. Rowland .:In Vitro BrdUrd Incorporation of Colorecttal Tumor Tissue in *Cell Prolif.* 26: 115–124 1983.

(List continued on next page.)

*Primary Examiner*—Nancy Degen
*Attorney, Agent, or Firm*—Skadden, Arps, Slate, Meagher & Flom LLP; Evelyn M. Sommer

[57] ABSTRACT

A method for detecting halogenated precursors incorporated into DNA is presented. The method is based on the selective photolysis of DNA by ultraviolet (UV) light at the sites of an incorporated halogenated precursor, such as the thymidine base analogs 5-bromo-2-deoxyuridine (BrdUrd), 5-iodo-2-deoxyuridine (IdUrd), 5-fluoro-2-deoxyuridine (FdUrd), or 5-chloro-2-deoxyuridine (CldUrd). The 3'-hydroxyl termini of the DNA single strand breaks generated during photolysis may be marked directly or indirectly with a fluorescent label. The DNA termini are directly labeled with fluorochrome-conjugated deoxyuridine triphosphate (dUTP) catalyzed by exogenous terminal deoxynucleotidyl transferase or DNA polymerase (nick translation system). The DNA termini are indirectly labeled with either biotin- or digoxygenin-conjugated dUTP; the incorporated biotin or digoxygenin is then detected following binding of fluorochrome-conjugated avidin or anti-digoxygenin antibody, respectively. The labeled DNA may be analyzed in situ by flow cytometry or fluorescence microscopy. Alternatively, the DNA may be isolated and analyzed by conventional methods, including gel electrophoresis and blotting assays, prior to marking with a flourescent label. The method does not require denaturation of the DNA and may be used with cells in suspension, thin tissue sections, bacteria, and viruses. The method has application in the analysis of cell proliferation and genotoxicity tests.

19 Claims, No Drawings

OTHER PUBLICATIONS deFazio, A. and M.H.N. Tattersall.:Rapid Fluorometric Detection of Drug Resistant Tumor Cells in *Br J. Cancer.* 52:633–636, 1985.

Takagi S., M.L. McFadden, R.E. Humphreys, B.A. Woda and T. Sairenji.:Detection of 5–Bromo–2–Deoxyuridine (BrdUred) Incorporation with Monoclonal Anti–BrdUrd Antibody After Deoxyribinuclease Treatment in *Cytometry.* 14:640–648, 1993.

Latt, S.A.:Detection of DNA Synthesis in Interphase Nuclei by Fluorescence Microscopy in *J. Cell Biol.* 62:546–560, 1974.

Darzynkiewicz, Z., F. Traganos and M., Melamed.:Distinction Betwen 5–Brmodeoxyuridine Labeled and Unlabeled Mitotic Cells by Flow Cytometry in *Cytometry,* 3:345–348, 1983.

Poot, M., M. Kubbies, H. Hoehn, A. Grossman, Y. Chen and P. Rabinovitch.:Cell Cycle Analysis Using Continuous Bromodeoxyuridine Labeling and Hoechst 33258–Ethidium Bromide Bivariate Floe Cytometry in *Meth Cell Biol.* 33:185–198, 1990.

Hutchinson, F.:The Lesions Produced by Ultraviolet Light in DNA Containing 5–Bromouracil in *Quart Rev Biophy.* 6:201–246, 1973.

Zwanenburg,T.S.B., A.A. van Zeeland and A.T. Natarajan.:Influence of Incorporated Broxodeoxyuridine on the Induction of Chromosomal Alterations by Ionizing Radiation and Long Wave UV in CHO Cells in *Mutation Res.* 150:283–292, 1985.

Gorczyca, W., S. Bruno, R.J. Darzynkiexicz, J. Gong and Z. Darzynkiewicz.:DNA Strand Breaks Occuring During Apoptosis:Their Early in Situ Detection by the Terminal Deoynucleotidyl Transferase and Nick Translation Assays and Prevention by Serine Protease Inhibitors in *Int. J. Oncol.* 1:639–648, 1992.

Gorczycz, W., J. Gong and Z. Darzynkiewicz.:Detection of DNA Strand Breaks in Individual Apoptotic Cells by the In Situ Terminal Deoxynucleotidyl Transferase and Nick Translation Assays in *Cancer Res.* 53:1945–1951, 1993.

Darzynkiewicz, Z., S. Bruno, G. Del Bino, W. Gorczyca, M.A. Hotz, P. Lassota and F. Traganos.:Features of Apoptotic Cells Measured by Flow Cyometry in *Cytometry,* 13:795–808, 1992.

Gong, J., F. Traganos and Z. Darzynkiewicz.:A Selective Procedure for DNA Extraction from Apoptotic Cells Applicable for Gel Electrophoresis and Flow Cytometry in *Anal Biochem* (in press).

Li, X., R. Patel, M.R. Melamed and Z. Darzynkiewicz.:The Cell Effects and Induction of Apoptosis by 5–Bromouridine in Cultures of Human Leukemic MOLT–4 and HL–60 Cell Lines and Mitogen Stimulated Normal Lymphocytes in *Cell Prolif* (in press).

Bino, G.D., J.S. Skierski and Z. Darzynkiewicz.:The Concentration–Dependent Diversity of Effects of DNA Topoisomerase I and II Inhibitors on the Cell Cycle of HL–60 Cells in *Experimental Cell Research.* 195:485–491, 1991.

Bruno, S. and Z. Darzynkiewicz.:Cell Cycle Dependent Expression and Stability of the Nuclear Protein Detected by Ki–67 Antibody in HL–60 Cells in *Cell Prolif.* 25:31–40, 1992.

Bruno, S., G.D. Bino, P. Lassota, W. Giaretti and Z. Darzynkiewicz.: Inhibitors of Proteases Prevent Endonucleolysis Accompanying Apoptotic Death of HL–60 Leukemic Cells and Normal Thymocytes in *Leukemia.* 6(11), 1113–1120, (Nov. 1992).

Compton, M.M.:A Biochemical Hallmark of Apoptosis:Internucleosomal Degradation of the Genome in *Cancer and Metastasis Reviews.* 11:105–119, 1992.

Chapman, R.S., C.M. Chresta, A.A. Herberg, H.M. Beere, S. Heer, A.D. Whetton, J.A. Hickman and C. Dive.:Further Characterisation of the In Situ Terminal Deoxynucleotidyl Transfferase (TdT) Assay for the Flow Cytometric Analysis of Apoptosis in Drug Resistant and Drug Sensitive Leukaemic Cells in *Cytometry.* 20:245–256, 1995.

Darzynkiewicz, Z., S. Bruno, G.D. Bino, W. Gorczyca, M.R. Hotz, P. Lassota and F. Traganos.:Features of Apoptotic Cells Measured by Flow Cytometry in *Cytometry.* 13:795–808, 1992.

Darzynkiewicz, Z.: Apoptosis in Antitumor Stratedies:Modulation of Cell Cycle or Differentiation in *Journal of Cellular Biochemistry.* 56:1–9, 1994.

Dive, C. C.D. Gregory, D.J. Phipps, D.L. Evans, A.E. Milner and A.H. Wyllie.:Analysis and Discrimination of Necrosis and Apoptosis (Programmed Cell Death) By Multiparameter Flow Cytometry in *Biochimica ett Biophysica Acta.* 1133:275–285, 1992.

Dolbeare, F. and J.R. Selden.:Immunochemical Quantitation of Bromodeoxyuridine:Application to Cell–Cycle Kinetics in *Methods In Cell Biology,* 41:297–316, 1994.

Gavrieli, Y., Y. Sherman and S.A. Ben–Sasson.:Identification of Programmed Cell Death In Situ via Specific Labeling of Nuclear DNA Fragmentation in *The Journal of Cell Biology,* 119(3):493–501, (November) 1992.

Gold, R., M. Schmied, G. Rothe, H. Zischler, H. Breitschopf, H. Wekerle and H. Lassmann.:Detection of DNA Fragmentation in Apoptosis: Application of In Situ Nick Translation to Cell Culture Systems and Tissue Sections in *The Journal of Histochemistry and Cytochemistry,* 41(7):1023–1030, 1993.

Gorczyca, W., K. Bigman, A. Mittelman, T. Ahmed, J. Gong, M.R. Melamed and Z. Darzynkiewicz.:Induction of DNA Strand Breaks Associates with Apoptosis during Treatment of Leukemias in *Leukemia.* 7(5):669–670, (May) 1993.

Hotz, M.A., F. Traganos and Z. Darzynkiewicz.:Changes in Nuclear Chromatin Related to Apoptosis or Necorosis Induced by the DNA Topoisomerase II Inhibitor Fostriecin in MOLT–4 and HL–60 Cells Are Revealed by Alered DNA Sensitivity to Denaturation in *Experimental Cell Research,* 201, 184–191, 1992.

Kamentsky, L.A. and L.D. Kamentsky.:Microscope–Based Multiparameter Laser Scanning Cytometer Yielding Data Comparable to Flow Cytometry Data in *Cytometry,* 12:381–387, 1991.

Koopman, G., C.P.M. Reutelingsperger, G.A.M. Kuitjen, R.M.J. Keehnen, S.T. Pais and M.H.J. van Oers.: Annexin V for Flow Cytometric Detection of Phosphatidylserine Expression on B Cells Undergoing Apoptosis in *Blood.* 84(5):1415–11420, (Sep. 1) 1994.

Xun., L., F. Traganos, M.R. Melamed and Z. Darzynkiewicz.:Detection of 5–Bromo–2–Deoxyuridine Incorporated into DNA by Labeling Strand Breaks Induced by Photolysis (SBIP) in *International Journal of Oncology,* 4:1157–1161, 1994.

Li, X., F. Traganos and Z. Darzynkiewiz.:Simultaneous Analysis o DNA Replication and Apoptosis during Treatment of HL-60 Cells with Camptothecin and Hyperthermia and Mitogen Stimulation of Human Lymphocytes in *Cancer Research.* 54:4289-4293, (Aug.) 1994.

Li, X. G. Jianping, E. Feldman, K. Seiter, F. Traganos and Z. Darzynkiewicz .: Apoptotic Cell Death During Treatment of Leukemias in *Leukemia and Lymphoma.* 13(1):65-70, 1994.

Li, X., F. Traganos, M.R. Melamed and Z. Darzynkiewicz.:Single-Step Procedure for Labeling DNA Strand Breaks with Flurorescein-or BODIPY-Conjugated Deoxynucleotides:Detection of Apoptosis and Bromodeoxyuridine Incorrporation in *Cytometry.* 20:172-180, 1995.

Nicoletti, I., G. Migliorati, M.C. Pagliacci, F. Grignani and C. Riccardi.:A Rapid and Simple Method for Measuring Thymocytte Apoptosis by Propidium Iodide Staining and Flow Cytometry in *Journal of Immunological Methods,* 139:271-279, 1991.

Raza, A., S. Gezer, S. Mundle, X.Z. Gao, S. Alvi, R. Borok, S. Rifkin, A. Ifükhar, V. Shetty, A. Parcharidou, J. Loew, B. Marcus, Z. Khan, C. Chaney, J. Showel, S. Gregory and H. Preisler.:Apoptosis in Bone Marrow Biopsy Samples Involving Stromal and Hematopietic Cells in 50 Patients with Myelodysplastic Syndromes in *Blood,* 86(1): 268-276, (Jul. 1) 1995.

P.R. Walker, V.M. Weaver, B. Lach, J. LeBlanc and M. Sikorska.:Endonuclease Activities Associates with High Molecular Weight and Internucleosomal DNA Fragmentation in Apoptosis in *Experimental Cell Research.* 213:100-106, 1994.

Wijsman, J.H., R.R. Jonker, R. Keijzer, C.J.H. Van De Velde, C.J. Cornelisse and J.H. Van Dierendonck.:A New Method to Detect Apoptosis in Paraffin Sections: In Situ End-Labeling of Fragmented DNA in *The Journal of Histochemistry and Cytochemistry,* 41(1):7-12, 1993.

Jirkowski, G.F, J.F. Ramalho-Ortigao, T. Lindl and H.Seliger.:Immunocytochemistry of 5-bromo-2'-deoxyuridine labelled oligonucleotide probes in Histo Chemistry, 91(1):51-53, 1989.

Jirkowski, G.F., J.F. Ramalho-Ortigao, K.W. Kesse and F. E. Bloom:In Situ Hybridization of Semithin Epon Sections with BrdU Labelled Oligonucleotide Probes in Histo Chemistry. 94(1):187-190, 1990.

DETECTION OF HALOGENATED PRECURSORS INCORPORATED INTO DNA

This application is a continuation of application Ser. No. 08/249,394 filed on May 26, 1994, now abandoned.

The United States may have certain rights to this invention under NIH Grant CA 28708.

BACKGROUND OF THE INVENTION

1. Field of the Invention

The present invention relates to the detection of DNA replication and DNA repair, and more particularly to the detection of halogenated precursors incorporated into the DNA.

2. Description of the Related Art

The process of DNA replication is studied primarily to assess the proliferative potential of cell populations and to study progression of the cell cycle. The study of cell proliferation has application in the prognosis of tumors and predictions of the likelihood of organ transplant rejection. In the process of DNA repair, DNA damage is detected and corrected; this process is studied mostly to evaluate the genotoxicity, i.e., mutagenicity and/or carcinogenicity, of environmental toxins and other substances.

There are two distinct methodologies currently used to analyze DNA replication or repair. One method is based on the incorporation of a radioactive DNA precursor, such as tritiated thymidine, into the repaired DNA molecules followed by autoradiographic detection or quantitation using a scintillation counter. This method is being phased out due to the ecological disadvantages associated with radioactive tracers and the cumbersome analysis of cells required by the autoradiography procedure.

The second method utilizes fluorescence rather than radioactivity. Most assays of this type are based on the detection of incorporated halogenated precursors, such as the thymidine base analogs 5-bromo-2-deoxyuridine (BrdUrd) or 5-iodo-2-deoxyuridine (IdUrd) (1,2). These assays are widely used in research laboratories and clinics. Their clinical usefulness is primarily in the evaluation of tumor prognosis; numerous observations indicate that the proportion of cells replicating DNA, or the potential doubling time of proliferating cells, has strong prognostic value (3–6).

BrdUrd is substituted stoichiometrically for thymidine in DNA molecules during the S-phase (synthesis phase) of the cell cycle. During the S-phase the cellular DNA content is doubling between the $G_1$ and $G_2$ cell phases (gap phases). The amount of incorporated BrdUrd is related to the new DNA content, i.e., the S-phase of the cell cycle.

The most common method of BrdUrd detection is based on the use of anti-BrdUrd antibodies (1,2). This conventional method, though proven to be of great value in numerous instances, has a serious drawback in that it requires DNA denaturation, i.e., strand separation, prior to incubation with the BrdUrd-specific antibody. This step is necessary to make the epitope, i.e., the incorporated precursor, accessible and reactive with the antibody. Denaturation involves either heat ($\geq 90°$ C.) or acid (2–4 M HCl) treatment. Under these conditions many cellular proteins undergo denaturation and/or extraction. The requirement for DNA denaturation makes it very difficult to combine the BrdUrd incorporation assay with other probes of cell phenotype or function, such as surface immunofluorescence, or the detection of intracellular antigens or other proteins. Furthermore, because of the differences in chromatin structure between different cell types, which in turn affect the DNA denaturation step, the BrdUrd antibody method fails when used in some clinical samples or cell lines. Several approaches designed to bypass the denaturation step, such as the partial digestion of DNA with nucleases, appear to be of limited practical value (7).

Alternative methods employing BrdUrd, based on the quenching of fluorochromes such as Hoechst 33258 (8) or acridine orange (9) by incorporated BrdUrd, are less sensitive compared to the assay which utilizes BrdUrd-specific antibody. Dye quenching methods have been used to detect cells that incorporated BrdUrd during continuous exposure to the precursor (10) but, because of their low sensitivity, have limited application, especially in the clinic.

The publications cited herein are incorporated by reference into this disclosure and appear in an Appendix to the application.

SUMMARY OF THE INVENTION

Accordingly, it is an object of the present invention to provide a method of detecting a halogenated precursor incorporated into DNA molecules under non-denaturing conditions as a measurement of DNA replication or DNA repair.

It is another object of the present invention to provide a sensitive method of detecting a halogenated precursor incorporated into DNA molecules as a measurement of DNA replication or DNA repair.

It is yet another object of the present invention to provide a method of detecting a halogenated precursor incorporated into DNA molecules which may be used in conjunction with, and without adversely affecting, other probes of cell phenotype or function.

It is a further object of the present invention to provide a method of detecting a halogenated precursor incorporated into DNA molecules which may be used in conjunction with, and without adversely affecting, methods of detecting intracellular antigens and other proteins.

It is yet a further object of the present invention to provide a method of detecting a halogenated precursor incorporated into DNA which may be used to simultaneously detect cells undergoing apoptosis, i.e., programmed cell death.

A still further object of the present invention to provide a method of detecting DNA replication which may be used as a tool to aid in the prognosis of tumors.

A final object of the present invention is to provide a method of detecting DNA repair as a tool for evaluating the genotoxicity, i.e., mutagenicity and/or carcinogenicity, of environmental toxins and other substances.

The invention is a method of detecting DNA replication or DNA repair through detection of halogenated precursors incorporated into DNA. The halogenated precursor is a thymidine base analog such as 5-bromo-2-deoxyuridine (BrdUrd), 5-iodo-2-deoxyuridine (IdUrd), 5-fluoro-2-deoxyuridine (FdUrd), or 5-chloro-2-deoxyuridine (CldUrd).

The preferred method comprises incorporating a halogenated precursor into DNA within cells; exposing the cells to ultraviolet (UV) light to induce photolysis of the DNA within the cells at the sites of precursor incorporation; fixing the cells; marking the photolysis-generated termini of the DNA with a fluorescent label using an exogenous enzyme to catalyze the labeling reaction; and detecting the fluorescence of the fluorescent-labeled DNA. The fluorescence may be detected in situ by flow cytometry or fluorescence microscopy, and is used to determine the amount of newly synthesized DNA in the cells and, thus, the current phase of the cell cycle. First, the amount of incorporated halogenated precursor is determined from the amount of fluorescence. Second, the amount of newly synthesized DNA within the cells is determined from the amount of incorporated halogenated precursor. Finally, the current phase of the cell cycle is determined from the amount of newly synthesized DNA. These determinations are accomplished using conventional methods well known to an ordinary person skilled in the art.

Another method comprises incorporating a halogenated precursor into DNA within biological entities, such as cells, bacteria, and viruses; exposing the biological entities to ultraviolet light to induce photolysis of the DNA within the biological entities at the sites of precursor incorporation; isolating the DNA from the biological entities; analyzing the isolated DNA; marking the photolysis-generated termini of the analyzed DNA with a fluorescent label; and detecting the fluorescence of the fluorescent-labeled DNA.

The present invention does not require denaturation of the DNA molecules since it is based upon fluorescent labeling of DNA single strand breaks at the sites of precursor incorporation which are induced by exposure to ultraviolet light, i.e., photolysis. This feature of the invention is a great advantage in that it allows the method to be used in conjunction with, and without adversely affecting, other probes of cell phenotype or function, and methods for detecting intracellular antigens and other proteins. In addition, the method can be used to simultaneously detect cells undergoing apoptosis, i.e., programmed cell death.

The above and numerous other objects of the invention that may be achieved by the preferred embodiment of the invention will be more readily understood from the following detailed description.

DESCRIPTION OF THE PREFERRED EMBODIMENT

A method for detecting a halogenated precursor incorporated into DNA as a measurement of DNA replication or DNA repair without denaturation of the DNA molecules is presented. The method may be used with cells in suspension, thin tissue sections, bacteria, and viruses. Examples of cells for which the method has been used include human leukemic HL-60 and MOLT 4 cell lines, normal human lymphocytes stimulated in vitro by the mitogen phytohemagglutinin, human leukemic bone marrow cells, and human breast carcinoma tissue.

This method may be employed to detect DNA replication in the analysis of cell proliferation. The most extensive application is expected to be in clinical oncology, where cell proliferation assays are used as prognostic markers of tumors. The method may also be used in monitoring tumor treatment efficiency, in cases in which the tumor can be sampled by venipuncture or bone marrow aspiration or biopsy (hematopoietic diseases) or by needle biopsy (solid tumors), for example, during treatment. In addition, the method may be employed to predict the likelihood of organ transplant rejection, i.e., to test for proliferation of the recipient's lymphocytes in the presence of specific donor cells.

The method does not require denaturation of the DNA molecules since it is based upon fluorescent labeling of DNA single strand breaks at the sites of precursor incorporation which are induced by exposure to ultraviolet light, i.e., photolysis. This feature allows the method to be used in conjunction with, and without adversely affecting, other probes of cell phenotype or function, and methods for detecting intracellular antigens and other proteins. In addition, the method can be used to simultaneously detect cells undergoing apoptosis, i.e., programmed cell death.

The method may also be used to detect DNA repair. Because several fluorescent labels may be attached at each DNA single strand break, i.e., at each site of incorporated precursor, the method is theoretically several times more sensitive than the conventional method based on the use of anti-BrdUrd antibodies. High sensitivity favors its use in tests of the mutagenicity of drugs, food components and additives, and environmental toxins, as a measurement of DNA repair replication.

The preferred method comprises incorporating a halogenated precursor into DNA within cells; exposing the cells to ultraviolet (UV) light to induce photolysis of the DNA within the cells at the sites of precursor incorporation; fixing the cells; marking the photolysis-generated termini of the DNA with a fluorescent label using an exogenous enzyme to catalyze the labeling reaction; and detecting the fluorescence of the fluorescent-labeled DNA. The fluorescence may be detected in situ by flow cytometry or fluorescence microscopy, and is used to determine the amount of newly synthesized DNA in the cells and, thus, the current phase of the cell cycle. First, the amount of incorporated halogenated precursor is determined from the amount of fluorescence. Second, the amount of newly synthesized DNA within the cells is determined from the amount of incorporated halogenated precursor. Finally, the current phase of the cell cycle is determined from the amount of newly synthesized DNA. These determinations are accomplished using conventional methods well known to an ordinary person skilled in the art.

The cells were exposed in vitro or in vivo to a halogenated precursor such as the thymidine base analogs 5-bromo-2-deoxyuridine (BrdUrd), 5-iodo-2-deoxyuridine (IdUrd), 5-fluoro-2-deoxyuridine (FdUrd), or 5-chloro-2-deoxyuridine (CldUrd), to effect the incorporation of the precursor into the DNA within the cells. In vivo exposure was accomplished by conventional intravenous, intramuscular, or intravesicular addition; these methods of incorporation are well known to an ordinary person skilled in the art. In vitro exposure was accomplished by incubation of the cells with the halogenated precursor. The cells were incubated with concentrations of precursor ranging from about 10 uM to about 50 uM, depending upon the type and physical state of the cells. Optimum incorporation into suspended cells was usually achieved with the lower concentrations of precursor, such as 10, 20, or 30 uM, whereas optimum incorporation into tissue sections usually required higher concentrations, such as 30, 40 or 50 uM. However, all five concentrations, i.e., 10, 20, 30, 40, and 50 uM, may be used for both suspended cells and tissue sections. The incubation periods ranged from about five minutes to about eight hours, again depending upon the type and physical state of the cells. Optimum incorporation into suspended cells was usually achieved with shorter incubation periods, such as five, thirty, or forty minutes, whereas optimum incorporation into tissue sections was usually achieved with longer incubation periods, such as one or two hours. The incubations were carried out at about 37° C. in the dark.

DNA in which a halogenated deoxynucleotide such as BrdUrd or IdUrd is substituted for thymidine is sensitive to illumination with UV light: absorption of high energy photons by such labeled DNA results in its photolysis or breakage (11, 12). Photons of approximately 310 nm wavelength are especially effective in causing DNA single strand breaks at sites of BrdUrd incorporation (11). Uniform illumination of DNA is expected to generate DNA single strand breaks in proportion to the amount of incorporated halogenated deoxynucleotide. It is believed that similar results will be obtained with DNA in which FdUrd or CldUrd is substituted for thymidine. It is also believed that incorporation studies involving FdUrd may provide an indirect indication of the sensitivity of various tumors to 5-fluorouracil (5-FU), the most widely used antitumor agent for the treatment of solid tumors. The method of the present invention may provide an accurate and sensitive technique for the detection of 5-FU in tumor cells. In addition, incorporation studies with FdUrd may provide insight into the mechanism of action of 5-FU.

It was determined that illumination of the cell suspension in Petri dishes or tissue sections on slides placed face down and positioned directly on the glass surface of a Foto UV Analytical DNA transilluminator (Fotodyne, Inc., New Berlin, Wis.) containing four 15 watt 300 nm bulbs and illuminated for approximately five minutes, was optimal in terms of induction of DNA single strand breaks in BrdUrd-labeled cells or tissue sections. An illumination period of approximately ten minutes was determined to be optimal for IdUrd-labeled cells. It is believed that similar results will be obtained with DNA in which FdUrd or CldUrd is substituted for thymidine.

Two variations of the preferred method exist with respect to the step for marking the 3'-hydroxyl termini of the photolysis-generated DNA strand breaks with a fluorochrome. Both direct and indirect marking procedures may be employed. In one embodiment, the DNA termini are directly labeled with a deoxynucleotide conjugated with a fluorochrome, such as fluorescein-conjugated deoxyuridine triphosphate (fluorescein-12-dUTP). In a second embodiment, the DNA termini were labeled with a deoxynucleotide conjugated with a first agent, such as biotinylated deoxyuridine triphosphate (b-dUTP) or digoxygenin-conjugated deoxyuridine triphosphate (d-dUTP), and thereafter incubated with a second agent conjugated with a fluorochrome, such as avidin-fluorescein isothiocyanate or fluorescein-conjugated anti-digoxygenin antibody, respectively, which binds to the first agent of the conjugated deoxynucleotide. An exogenous enzyme such as terminal deoxynucleotidyl transferase or DNA polymerase (nick translation system) is used to catalyze the labeling reaction in both variations.

Another method comprises incorporating a halogenated precursor into DNA within biological entities, such as cells, bacteria, and viruses; exposing the biological entities to ultraviolet light to induce photolysis of the DNA within the biological entities at the sites of precursor incorporation; isolating the DNA from the biological entities; analyzing the isolated DNA; marking the photolysis-generated termini of the analyzed DNA with a fluorescent label; and detecting the fluorescence of the fluorescent-labeled DNA. The incorporation step is accomplished by exposing the biological entities in vitro to the halogenated precursor, which is a thymidine base analog such as BrdUrd, IdUrd, FdUrd, or CldUrd. In vitro exposure is accomplished by incubation of the biological entities with the precursor. Isolation of the DNA from the biological entities is accomplished using conventional methods, such as extraction, which are well known to an ordinary person skilled in the art. Analysis of the isolated DNA is accomplished by conventional methods such as gel electrophoresis and blotting assays, which are well known to an ordinary person skilled in the art. The photolysis-generated termini of the analyzed DNA are marked with a fluorescent label using the methods described herein or using conventional methods well known to an ordinary person skilled in the art. The fluorescence of the fluorescent-labeled DNA is detected using methods well known to an ordinary person skilled in the art.

The following examples will serve to illustrate the present invention but are in no way intended to limit the scope of the invention which is defined in the appended claims. The materials and methods presented in the examples are cited in previous publications (13, 14).

EXAMPLE 1

Cells. Human leukemic HL-60 cell lines were maintained in RPMI 1640 medium (Gibco BRL Life Technologies, Inc., Grand Island, N.Y.) supplemented with ten percent fetal calf serum, 100 units/ml penicillin, 100 ug/ml streptomycin and 2 mM L-glutamine. The cells were split every third day and were diluted 1:2 one day before each experiment. Cell densities in cultures did not exceed $5 \times 10^5$ cells/ml.

Precursor Incorporation. The cells were incubated with 10 uM BrdUrd (Sigma Chemical Co., St. Louis, Mo.) at 37° C. in the dark for one hour.

Photolysis. At the end of the incubation period, the cells were illuminated with ultraviolet (UV) light of 310 nm wavelength for five minutes.

Cell Fixation. The cells were rinsed in phosphate buffered saline (PBS) and fixed in 70% ethanol. In some experiments, the cells were also fixed in 1% formaldehyde (pH 7.4) at 0°–4° C. for 15 minutes, and then post-fixed and stored in 70% ethanol.

Fluorochrome Labeling. The 3'-hydroxyl termini of the DNA single strand breaks generated by photolysis were labeled with digoxygenin-conjugated deoxyuridine triphosphate (d-dUTP) followed by incubation with an fluorochrome-conjugated anti-digoxygenin antibody. This was accomplished using the commercial kit for DNA strand break labeling developed to identify apoptotic cells (ApopTag™ kit, ONCOR Inc., Gaithersburg, Md.), according to the protocol included with the kit by the vendor.

Flow Cytometry. The cells were rinsed in PBS with 0.1% Triton-X 100 and resuspended in 1 ml of PBS containing 5 ug/ml of propidium iodide (PI) and 0.1% RNase A (both from Sigma Chemical Company). Flow cytometry was performed on a FACScan Flow Cytometer (Becton Dickinson, San Jose, Calif.) The red (PI) and green (fluorescein) fluorescence emissions from each cell were separated and measured using the standard optics of the FACScan. The data from $10^4$ cells per sample were collected, stored, and analyzed using LYSIS II software (Bectin-Dickinson). The signals of green fluorescence were measured using both linear and logarithmic amplification for each sample.

EXAMPLE 2

Human leukemic HL-60 cells were cultured as in Example 1. The cells were incubated with 10 uM IdUrd (Sigma Chemical Co., St. Louis, Mo.) at 37° C. in the dark for one hour. The cells were photolysed for ten minutes and fixed as before. The 3'-hydroxyl termini of the DNA strand breaks generated by photolysis were labeled with d-dUTP as before. Fluorescence of individual cells was measured by flow cytometry as before.

EXAMPLE 3

Human leukemic HL-60 cells were cultured, incubated with 10 uM BrdUrd, photolysed, and fixed as in Example 1.

The 3'-hydroxyl termini of the DNA single strand breaks generated by photolysis were labeled directly with fluorochrome-conjugated dUTP (fluorescein-12-dUTP) (Boehringer Mannheim Biochemicals, Indianapolis, Ind.). Fluorescence of individual cells was measured by flow cytometry as before.

EXAMPLE 4

Human leukemic HL-60 cells are cultured, labeled with 10 uM BrdUrd, photolysed, and fixed as described in Example 1.

Fluorochrome Labeling. The 3'-hydroxyl termini of the DNA single strand breaks generated by photolysis are labeled with biotinylated dUTP (b-dUTP) followed by incubation with fluorochrome-coupled avidin. Two procedures are followed, each using a different exogenous enzyme to catalyze the addition of dUTP to the DNA termini:

(1) TdT Assay. After fixation and washing, cells are resuspended in 50 ul of a solution containing 0.1M sodium cacodylate (pH 7.0) (Sigma), 1 mM $CoCl_2$ (Sigma), 0.1 mM dithiothreitol (Sigma), 0.05 mg/ml bovine serum albumin (Sigma), 10 units of terminal deoxynucleotidyl transferase (Boehringer Mannheim), and 0.5 nmoles biotin-16-dUTP (TdT buffer). In some experiments, in addition to b-dUTP, unlabeled dATP, dGTP, and dCTP are included, each at a concentration of 20 uM. The cells are incubated in this solution at 37° C., for time intervals between 15 minutes and 3 hours, rinsed in PBS, and resuspended in 100 ul of the staining buffer containing fluoresceinated avidin, which contains 2.5 ug/ml fluoresceinated avidin, 4× saline-sodium citrate buffer (Sigma) (1×SSC=0.15 M NaCl, 0.015 M Na-citrate), 0.1% Triton X-100, and 5% (w/v) nonfat dry milk. Cells are incubated with this buffer for 30 minutes at room temperature in the dark. The TdT assay is also performed on cytospin preparations on slides. The specimens are fixed for 15 minutes in 1% formaldehyde in PBS (pH 7.4), rinsed in PBS, and transferred to 70% ice-cold ethanol for 1 hour. After rinsing in PBS, excess PBS is removed, and 25 ul of TdT buffer are pipeted onto slides. The specimens are kept in a humidified chamber for 30 minutes at 37° C. The slides are then rinsed in PBS and incubated in the dark for 30 minutes with the staining buffer. Nucleotides, biotin-16-dUTP, avidin-fluorescein isothiocyanate, terminal deoxynucleotide transferase, and DNA-polymerase were purchased from Boehringer-Mannheim Biochemicals.

(2) NT Assay. Following fixation, the cells are rinsed once with PBS, and 2×10$^5$ cells are suspended in 12.5 ul of nick translation buffer consisting of 2.5 $MgCl_2$, 10 mM B-mercaptoethanol (Bio-Rad Laboratories, Richmond, Calif.), 50 mM Tris (pH 7.8), 10 ug/ml bovine serum albumin, 1 unit *E. coli* DNA polymerase, 0.2 nmoles unlabeled DATP, dGTP, and dCTP, and 0.2 nmoles biotin-16-dUTP. The cells are incubated in nick translation buffer with gentle agitation every 15 minutes, at 15° C., for up to 6 hours. Afterward, the cells are washed in PBS and resuspended in 100 ul of the staining buffer described above.

Fluorescence of individual cells is measured by flow cytometry as before.

EXAMPLE 5

Human leukemic HL-60 cells are cultured, labeled with 10 uM IdUrd, photolysed, and fixed as described in Example 2 above. The 3'-hydroxyl termini of the DNA single strand breaks generated by photolysis are labeled with biotinylated dUTP (b-dUTP) followed by incubation with fluorochrome-coupled avidin as before. Fluorescence of individual cells is measured by flow cytometry as before.

EXAMPLE 6

Human breast carcinoma tissue was labeled by incubating thin (≦1 mm) slices of freshly resected tumor in RPMI 1640 medium, with 30 uM BrdUrd for one hour at 37° C. The tissue was then fixed overnight in 70% ethanol, embedded in paraffin and sectioned. The sections on slides were deparaffinized and rehydrated. The slides were placed face down on the illuminator and exposed to UV light for five minutes. The 3'-hydroxyl termini of the DNA single strand breaks generated by photolysis were labeled with d-dUTP, followed by incubation with a fluorochrome-conjugated antibody as in Example 1. Nuclei were counterstained on slides with propidium iodide. In preparations viewed under a Nikon epifluorescence microscope, BrdUrd-labeled nuclei fluoresced green while nuclei which had not incorporated the precursor fluoresced red.

EXAMPLE 7

Human breast carcinoma tissue is quick frozen in liquid nitrogen, sliced into thin slices, and mounted on a slide, i.e., a frozen section is prepared. The tissue is incubated with BrdUrd, photolysed, and fixed as in Example 6. The 3'-hydroxyl termini of the DNA single strand breaks generated by photolysis are labeled with d-dUTP, followed by incubation with a fluorochrome-conjugated antibody as in Example 1. Fluorescence microscopy is done as in Example 6.

EXAMPLE 8

An "imprint" of human breast carcinoma tissue is prepared by making a clean slice through the tumor and pressing the sliced tumor onto a glass slide to leave an imprint of the tumor consisting of a layer of cells. The slide is incubated with BrdUrd, photolysed, and fixed as in Example 7. The 3'-hydroxyl termini of the DNA single strand breaks generated by photolysis are labeled with d-dUTP, followed by incubation with a fluorochrome-conjugated antibody as in Example 1. Fluorescence microscopy is done as in Example 6.

EXAMPLE 9

Human breast carcinoma tissue is labeled by incubating thin (≦1 mm) slices of freshly resected tumor in RPMI 1640 medium, with 20 uM IdUrd for one hour at 37° C. The tissue is then fixed, and sections are prepared, treated and photolysed as in Example 6 above. The 3'-hydroxyl termini of the DNA single strand breaks generated by photolysis are labeled with d-dUTP, followed by incubation with a fluorochrome-conjugated antibody as in Example 1. Fluorescence microscopy is done as in Example 6.

EXAMPLE 10

Human breast carcinoma tissue is labeled with 10 uM BrdUrd, fixed and photolysed as described in Example 6 above. The 3'-hydroxyl termini of the DNA single strand breaks generated by photolysis are labeled with biotinylated dUTP (b-dUTP) followed by incubation with fluoresceinated avidin as in Example 4 above. Fluorescence microscopy is done as in Example 6.

EXAMPLE 11

Human breast carcinoma tissue is labeled with 20 uM IdUrd, fixed and photolysed as described in Example 9 above. The 3'-hydroxyl termini of the DNA single strand breaks generated by photolysis are labeled with biotinylated dUTP (b-dUTP) followed by incubation with fluoresceinated avidin as in Example 4 above. Fluorescence microscopy is done as in Example 6.

Plots may be made of DNA content versus BrdUrd incorporation in a comparison of the results obtained using the present invention and the conventional immunocytochemical detection method, i.e., the anti-BrdUrd antibody method. Exponentially growing HL-60 cells were incubated in the presence of 50 um BrdUrd for one hour. The incorporated BrdUrd was detected either immunocytochemically, denaturing the DNA with 2.0M HCl and using the anti-BrdUrd antibody as described elswhere (17) or using the method of the present invention, without DNA denaturation. Cellular DNA was counterstained with PI to identify the cell cycle position. In both techniques, only the cells with a DNA content equivalent to that of S-phase cells were labeled; the cells that were not incubated with BrdUrd, i.e., control cells, remained unlabeled. The labeling of S-phase cells was very intensive by both assays, as may be noted by the exponential scale of the green fluorescence. The results obtained with the method of the present invention were similar to those obtained with the conventional immunocytochemical method.

Plots may be made of DNA content versus dUTP incorporation for cells following incorporation of either BrdUrd or IdUrd. Cells were incubated with 10 uM BrdUrd or IdUrd for 1 hour, washed, fixed and either illuminated with UV light or left unilluminated. The samples were then exposed to d-dUTP in the presence of TdT. Only those cells exposed to UV light incorporated dUTP into S-phase cells, which could be unambiguously identified in the two-parameter plots. Similar results were obtained using either BrdUrd or IdUrd.

The advantages of the present invention are numerous. First, the method does not require denaturation of the DNA molecules. This feature allows the method to be used in conjunction with, and without adversely affecting, other probes of cell phenotype or function, and with methods for detecting intracellular antigens and other proteins. Second, the method is sensitive. Finally, the method may be used as a tool to aid in the prognosis of tumors and evaluation of potential genotoxins, i.e., mutagens and/or carcinogens. Many variations will be apparent to those skilled in the art. It is therefore to be understood that, within the scope of the appended claims, the invention may be practiced other than as specifically described.

APPENDIX

1. Gratzner H. G., Monoclonal antibody to 5-bromodeoxyuridine. A new reagent for detection of DNA replication. Science 218: 474–475, 1982.
2. Dolbeare F., Gratzner H. G., Pallavicini M. G., Gray J. W., Flow cytometric measurement of total DNA content and incorporated bromodeoxyuridine. Proc Natl Acad Sci USA 80: 5573–5577, 1983.
3. Begg A. C., Menally N. J., Shrieve D. C., Karchner H., A method to measure the duration of DNA synthesis and the potential doubling time from a single sample. Cytometry 6: 620–626, 1985.
4. Falini B., Canino S., Sacchi S., Ciani C., Martelli M. F., Gerdes J., Stein H., Pileri S., Gobbi M., Fagioli M., Minelli O., Flenghi L. Immunocytochemical evaluation of the percentage of proliferating cells in pathological bone marrow and peripheral blood samples with the Ki-67 and anti-bromodeoxyuridine antibodies. Br J Hematol 69: 311–320, 1988.
5. Williamson K., Halliday I., Hamilton P., Ruddell J., Varma M., Maxwell P., Crockard A., Rowland B., In vitro BrdUrd incorporation of colorectal tumour tissue. Cell Prolif 26: 115–124, 1993.
6. deFazio A., Tattersall M. H. N., Rapid fluorometric detection of drug resistant tumor cells. Br J Cancer 52: 633–636, 1985.
7. Takagi S., McFadden M. L., Humphreys R. E., Woda B. A., Sairenji T, Detection of 5-bromo-2-deoxyuridine (BrdUrd) incorporation with monoclonal anti-BrdUrd antibody after deoxyribinuclease treatment. Cytometry 14: 640–648, 1993.
8. Latt S. A., Detection of DNA synthesis in interphase nuclei by fluorescence microscopy. J. Cell Biol. 62:546–560, 1974.
9. Darzynkiewicz Z., Traganos F., Melamed M. R., Distinction between 5-brmodeoxyuridine labeled and unlabeled mitotic cells by flow cytometry. Cytometry 3: 345–348, 1983.
10. Poot M., Kubbies M., Hoehn H., Grossman A., Chen Y., Rabinovitch P., Cell cycle analysis using continuous bromodeoxyuridine labeling and Hoechst 33258-ethidium bromide bivariate floe cytometry. Meth Cell Biol 33: 185–198, 1990.
11. Hutchinson F., The lesions produced by ultraviolet light in DNA containing 5-bromouracil. Quart Rev Biophy 6: 201–246, 1973.
12. Zwanenburg T. S. B., van Zeeland A. A., Natarajan A. T., Influence of incorporated bromodeoxyuridine on the induction of chromosomal alterations by ionizing radiation and long wave UV in CHO cells. Mutation Res 150: 283–292, 1985.
13. Gorczyca W., Bruno S., Darzynkiexicz R. J., Gong J., Darzynkiewicz Z, DNA strand breaks occurring during apoptosis: their early in situ detection by the terminal deoynucleotidyl transferase and nick translation assays and prevention by serine protease inhibitors. Int. J Oncol 1: 639–648, 1992.
14. Gorczyca W., Gong J., Darzynkiewicz Z, Detection of DNA strand breaks in individual apoptotic cells by the in situ terminal deoxynucleotidyl transferase and nick translation assays. Cancer Res 52: 1945–1951, 1993.
15. Darzynkiewicz Z., Bruno S., Del Bino G., Gorczyca W., Hotz M. A., Lassota P., Traganos F., Features of apoptotic cells measured by flow cytometry. Cytometry 13: 795–808, 1992.
16. Gong J., Traganos F., Darzynkiewicz Z., A selective procedure for DNA extraction from apoptotic cells applicable for gel electrophoresis and flow cytometry. Anal Biochem (in press).
17. Li X, Patel R, Melamed M. R., Darzynkiewicz Z., The cell cycle effects and induction of apoptosis by 5-bromouridine in cultures of human leukemic MOLT-4 and HL-60 cell lines and mitogen stimulated normal lymphocytes. Cell Prolif (In press).

What is claimed as new and desired to be secured by Letters Patent of the United States is:

1. A method for determining the phase of cell cycle in a sample of cells, comprising the steps of:
   (a) exposing a sample of cells to a halogenated precursor under conditions appropriate to incorporate the precursor into the DNA within the cells of the sample which cells are replicating DNA;
   (b) exposing the cells to ultraviolet light to induce photolysis of the DNA within the cells at the site of the precursor incorporation so as to generate a single DNA strand break containing a terminus at the sites;

(c) fixing the cells;

(d) exposing the cells to a deoxynucleotide associated with a fluorochrome which deoxynucleotide is capable of binding specifically to the terminus and to an exogenous enzyme catalyzing such binding under conditions such that the deoxynucleotide binds to the DNA at the terminus;

(e) detecting the fluorescence of the labelled DNA within the cells;

(f) determining the amount of the incorporated precursor within the DNA from the amount of the fluorescence detected;

(g) determining the amount of newly synthesized DNA in the cells from the amount of the incorporated precursor; and (h) determining the phase of the cell cycle from the amount of newly synthesized DNA.

2. A method for detecting halogenated precursors incorporated into DNA as recited in claim 1, wherein the incorporating step is accomplished by exposing said cells in vitro to said halogenated precursor.

3. A method for detecting halogenated precursors incorporated into DNA, comprising the steps of:

(a) exposing a sample of cells to a halogenated precursor under conditions appropriate to incorporate the precursor into newly synthesized DNA within the cells;

(b) exposing the cells to ultraviolet light to induce photolysis of the DNA within the cells at the site of the precursor incorporation so as to generate a single DNA strand break containing a terminus at the site;

(c) fixing the cells;

(d) exposing the cells to a deoxynucleotide associated with a fluorochrome which deoxynucleotide is capable of specifically binding to the terminus and to an exogenous enzyme catalyzing such binding under conditions such that the deoxynucleotide binds to the DNA at the terminus;

(e) detecting the fluorescence of the labelled DNA within the cells; and (f) determining the amount of the incorporated precursor within the DNA from the amount of the fluorescence detected.

4. A method of claim 3 wherein the deoxynucleotide associated with a fluorochrome is directly conjugated to the fluorochrome.

5. A method of claim 3 wherein the deoxynucleotide associated with a fluorochrome is directly conjugated to a first agent and is then exposed to a second agent coupled to a fluorochrome, which second agent has an affinity for the first agent and binds thereto.

6. A method for detecting halogenated precursors incorporated into DNA as recited in claim 5, wherein said deoxynucleotide is deoxyuridine triphosphate.

7. A method for detecting halogenated precursors incorporated into DNA as recited in claim 5, wherein said exogenous enzyme is selected from the group consisting of terminal deoxynucleotidyl transferase and DNA polymerase.

8. A method for detecting halogenated precursors incorporated into DNA as recited in claim 3, wherein said halogenated precursor is a thymidine base analog selected from the group consisting of 5-bromo-2-deoxyuridine, 5-iodo-2-deoxyuridine, 5fluoro-2-deoxyuridine, and 5-chloro-2-deoxyuridine.

9. A method for detecting halogenated precursors incorporated into DNA as recited in claim 3, wherein said ultraviolet light comprises photons of approximately 310 nm wavelength.

10. A method for detecting halogenated precursors incorporated into DNA as recited in claim 3, wherein said fixing step is accomplished using ethanol.

11. A method for detecting halogenated precursors incorporated into DNA as recited in claim 3, wherein said detection is accomplished by passing said cells through a flow cytometer.

12. A method for detecting halogenated precursors incorporated into DNA as recited in claim 3, wherein said detection is accomplished by means of a fluorescence microscope.

13. A method for detecting halogenated precursors incorporated into DNA as recited in claim 3, wherein said deoxynucleotide is deoxyuridine triphosphate.

14. A method for detecting halogenated precursors incorporated into DNA as recited in claim 3, wherein said exogenous enzyme is selected from the group consisting of terminal deoxynucleotidyl transferase and DNA polymerase.

15. A method for detecting halogenated precursors incorporated into DNA of a biological entity, wherein the biological entity is a cell, a bacterium or a virus, comprising the steps of:

(a) exposing the biological entity to a halogenated precursor under conditions appropriate to incorporate the precursor into newly synthesized DNA of the biological entity;

(b) exposing the biological entity to ultraviolet light to induce photolysis of the DNA within the biological entity at the site of the precursor incorporation so as to generate a single DNA strand break containing a terminus at the site;

(c) isolating the DNA from the biological entity;

(d) analyzing the DNA;

(e) exposing the DNA to a deoxynucleotide associated with a fluorochrome which deoxynucleotide is capable of binding specifically to the terminus and to an exogenous enzyme catalyzing such binding under conditions such that the deoxynucleotide binds to the DNA at the terminus; and (f) detecting the fluorescence of the labelled DNA, thereby detecting the amount of the incorporated precursor within the DNA of the biological entity.

16. A method for detecting halogenated precursors incorporated into DNA as recited in claim 15, wherein the incorporating step is accomplished by exposing said biological entity in vitro to said halogenated precursor.

17. A method for detecting halogenated precursors incorporated into DNA as recited in claim 15, wherein said halogenated precursor is a thymidine base analog selected from the group consisting of 5-bromo-2-deoxyuridine, 5-iodo-2-deoxyuridine, 5-fluoro-2-deoxyuridine, and 5-chloro-2-deoxyuridine.

18. A method for detecting halogenated precursors incorporated into DNA as recited in claim 15, wherein said analyzing step comprises a gel electrophoresis method.

19. A method for detecting halogenated precursors incorporated into DNA as recited in claim 15, wherein said analyzing step comprises a blotting method.

\* \* \* \* \*